(12) United States Patent
Farin et al.

(10) Patent No.: US 9,282,879 B2
(45) Date of Patent: Mar. 15, 2016

(54) LAPAROSCOPE SYSTEM

(75) Inventors: Danny Farin, Hod-Hasharon (IL); Yehuda Bachar, Givat-Shmuel (IL)

(73) Assignee: EON SURGICAL LTD., Tel-Aviv (IL)

( * ) Notice: Subject to any disclaimer, the term of this patent is extended or adjusted under 35 U.S.C. 154(b) by 0 days.

(21) Appl. No.: 14/006,938

(22) PCT Filed: Mar. 21, 2012

(86) PCT No.: PCT/EP2012/055041
§ 371 (c)(1),
(2), (4) Date: Nov. 18, 2013

(87) PCT Pub. No.: WO2012/126967
PCT Pub. Date: Sep. 27, 2012

(65) Prior Publication Data
US 2014/0066711 A1 Mar. 6, 2014

Related U.S. Application Data

(60) Provisional application No. 61/466,960, filed on Mar. 24, 2011.

(51) Int. Cl.
*A61B 1/04* (2006.01)
*A61B 1/00* (2006.01)
(Continued)

(52) U.S. Cl.
CPC .......... *A61B 1/00121* (2013.01); *A61B 1/0011* (2013.01); *A61B 1/00105* (2013.01); *A61B 1/04* (2013.01); *A61B 1/053* (2013.01); *A61B 1/0676* (2013.01); *A61B 1/3132* (2013.01); *A61B 19/5212* (2013.01); *A61B 1/00124* (2013.01); *A61B 17/34* (2013.01);
(Continued)

(58) Field of Classification Search
USPC .............................. 600/109, 160; 29/428, 825
See application file for complete search history.

(56) References Cited

U.S. PATENT DOCUMENTS 5,375,588 A 12/1994 Yoon
5,441,059 A * 8/1995 Dannan ......................... 128/898
(Continued)

FOREIGN PATENT DOCUMENTS

CN 101322638 A 12/2008
CN 103220987 A 7/2013
(Continued)

OTHER PUBLICATIONS

International Search Report mailed Jan. 21, 2013, as received in corresponding International Application No. PCT/EP2012/055041.
(Continued)

*Primary Examiner* — Matthew J Kasztejna
(74) *Attorney, Agent, or Firm* — Baker and Hostetler LLP

(57) ABSTRACT

A visual system for laparoscopy comprising a visual device having a visual head member and an elongated connector; a manipulation device having a handheld operation portion, an insertion portion and a first contact element; and an external device comprising means to communicate with the vision head member, via the first contact element, when the elongated connector is mounted in an lumen of the insertion portion. The insertion portion of the manipulation device is configured to be extendable out from a body cavity through an airtight passage whereby the elongated connector is configured to be slidably mounted into the lumen of the insertion portion outside of the body cavity upon the insertion portion is withdrawn into the body cavity.

20 Claims, 7 Drawing Sheets

(51) Int. Cl.
*A61B 1/05* (2006.01)
*A61B 1/06* (2006.01)
*A61B 1/313* (2006.01)
*A61B 19/00* (2006.01)
*A61B 17/34* (2006.01)
*A61B 17/00* (2006.01)

(52) U.S. Cl.
CPC .............. *A61B 2017/00473* (2013.01); *A61B 2017/00477* (2013.01); *A61B 2019/521* (2013.01); *A61B 2019/5206* (2013.01); *Y10T 29/49117* (2015.01); *Y10T 29/49826* (2015.01)

(56) References Cited

U.S. PATENT DOCUMENTS

| | | | |
|---|---|---|---|
| 5,980,493 A | 11/1999 | Smith et al. | |
| 6,095,970 A * | 8/2000 | Hidaka et al. | 600/110 |
| 6,146,402 A | 11/2000 | Munoz | |
| 6,387,043 B1 | 5/2002 | Yoon | |
| 7,316,699 B2 | 1/2008 | McFarlane | |
| 7,593,777 B2 | 9/2009 | Gerber | |
| 8,002,764 B2 * | 8/2011 | High | 604/506 |
| 8,225,798 B2 * | 7/2012 | Baldwin et al. | 128/898 |
| 2005/0234294 A1 | 10/2005 | Saadat et al. | |
| 2006/0025651 A1 | 2/2006 | Adler et al. | |
| 2007/0073323 A1 | 3/2007 | Carter et al. | |
| 2008/0015413 A1 * | 1/2008 | Barlow et al. | 600/114 |
| 2008/0249363 A1 | 10/2008 | Nakamura et al. | |
| 2008/0309758 A1 | 12/2008 | Karasawa et al. | |
| 2010/0298774 A1 * | 11/2010 | Igov | 604/164.01 |
| 2011/0046440 A1 | 2/2011 | Asada et al. | |
| 2011/0087267 A1 * | 4/2011 | Spivey et al. | 606/205 |
| 2011/0208007 A1 * | 8/2011 | Shohat et al. | 600/227 |
| 2012/0083826 A1 * | 4/2012 | Chao et al. | 606/205 |

FOREIGN PATENT DOCUMENTS

| | | |
|---|---|---|
| JP | 2002-514448 A | 5/2002 |
| WO | 99/58044 A1 | 11/1999 |
| WO | 2010/144219 A1 | 12/2010 |
| WO | 2012/035524 A2 | 3/2012 |

OTHER PUBLICATIONS

International Preliminary Report on Patentability mailed Sep. 24, 2013, as received in corresponding International Application No. PCT/EP2012/055041.

* cited by examiner

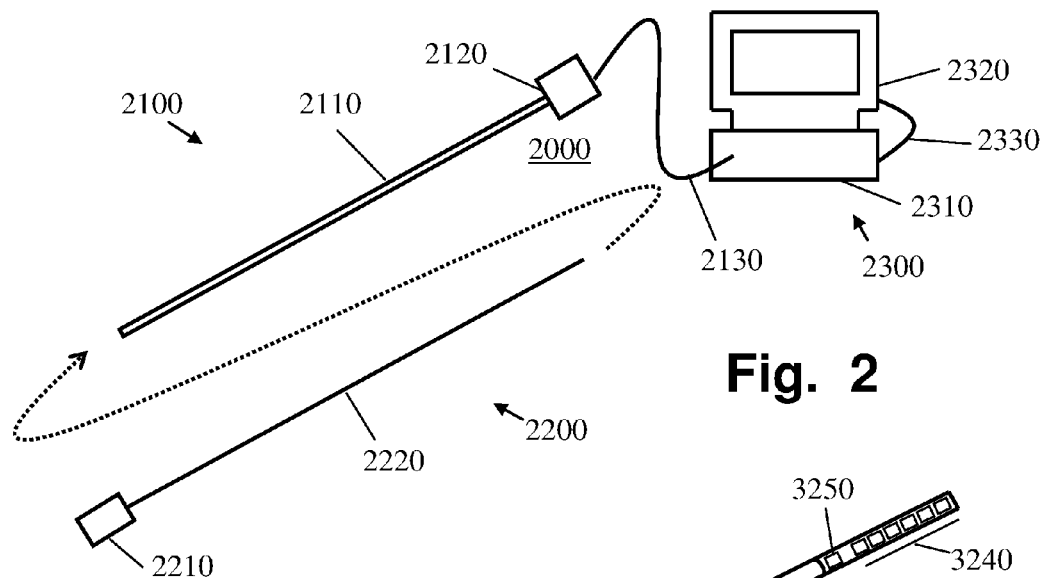
Fig. 2
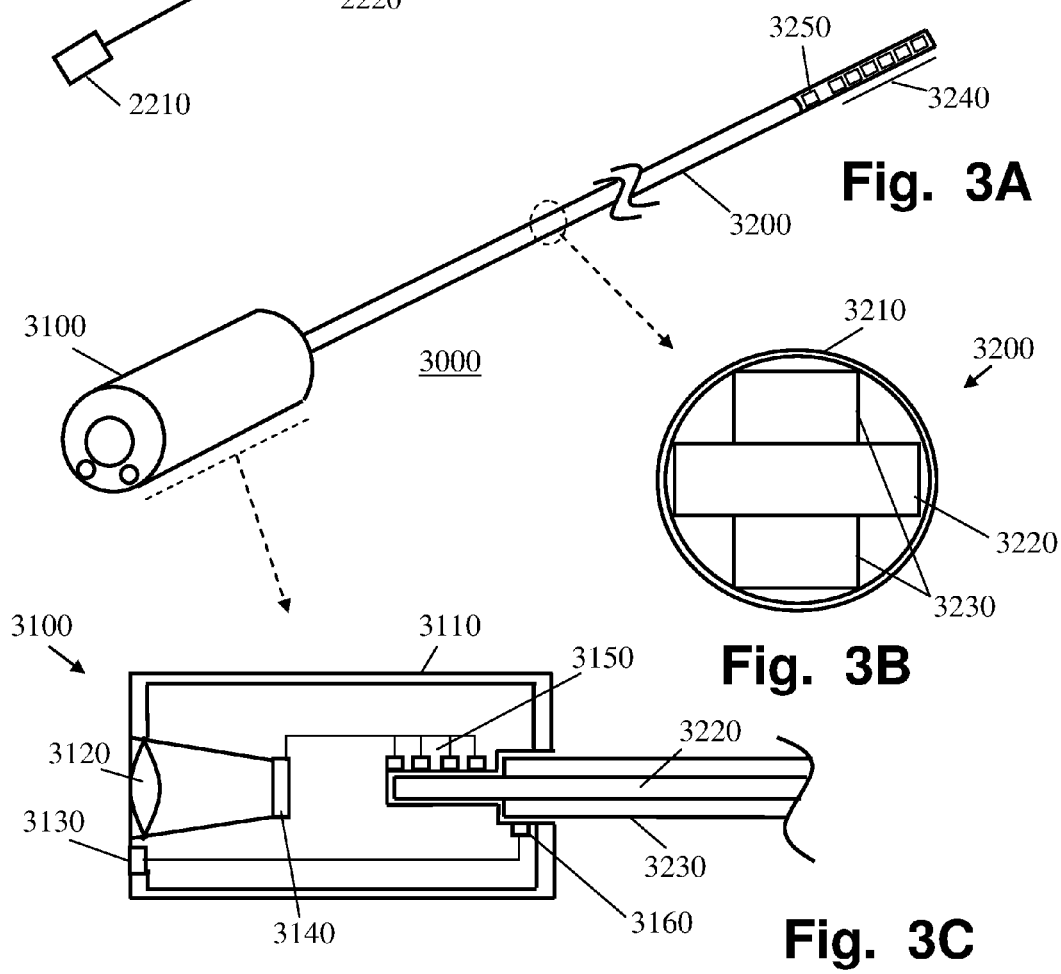
Fig. 3A
Fig. 3B
Fig. 3C

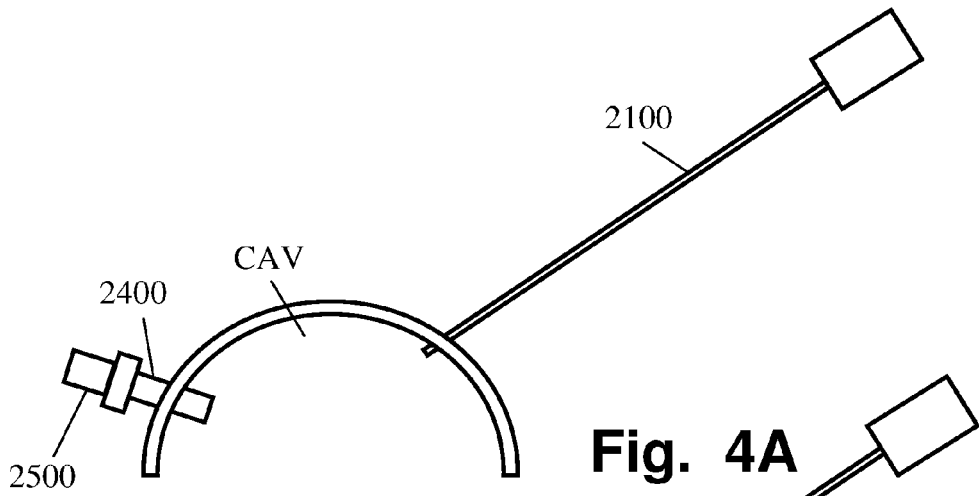
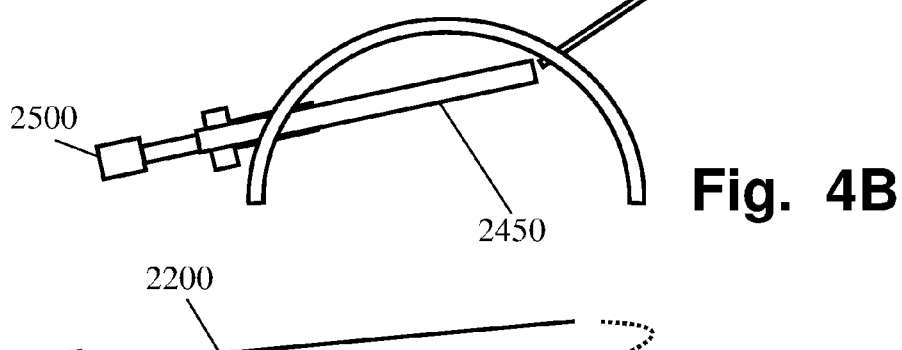
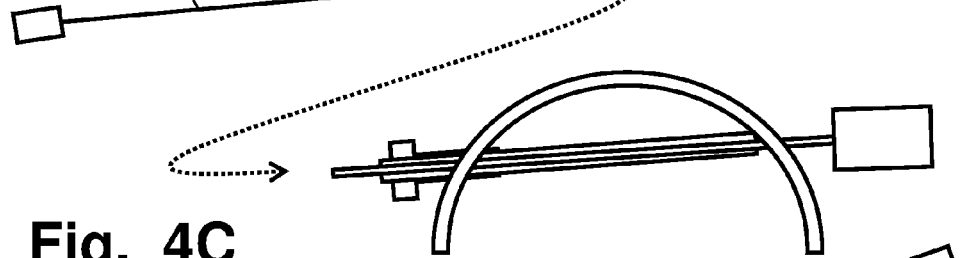
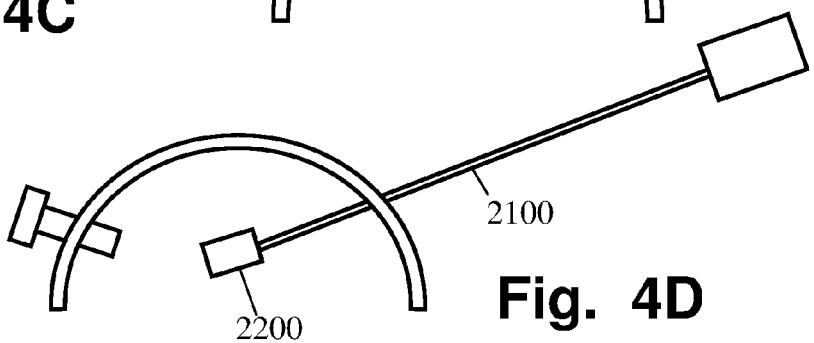

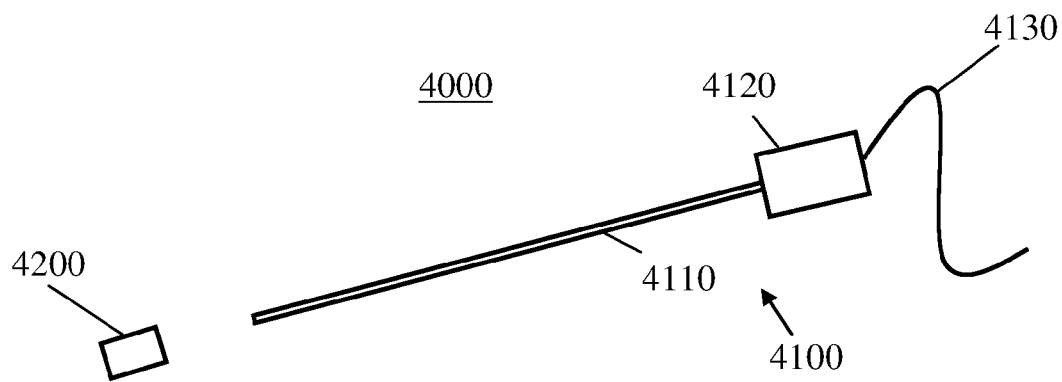
Fig. 5
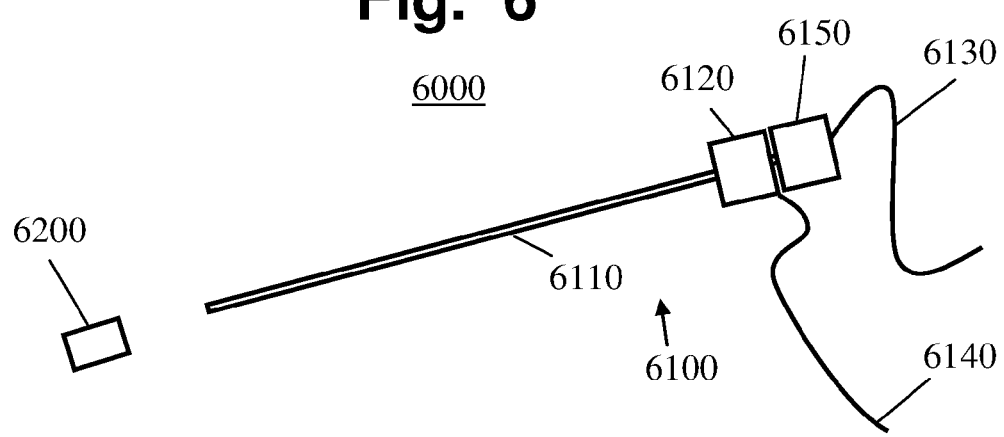
Fig. 6
Fig. 7

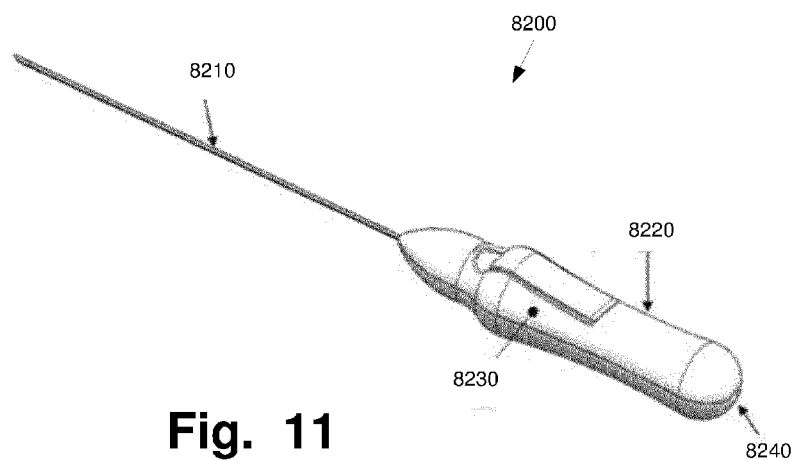
Fig. 11
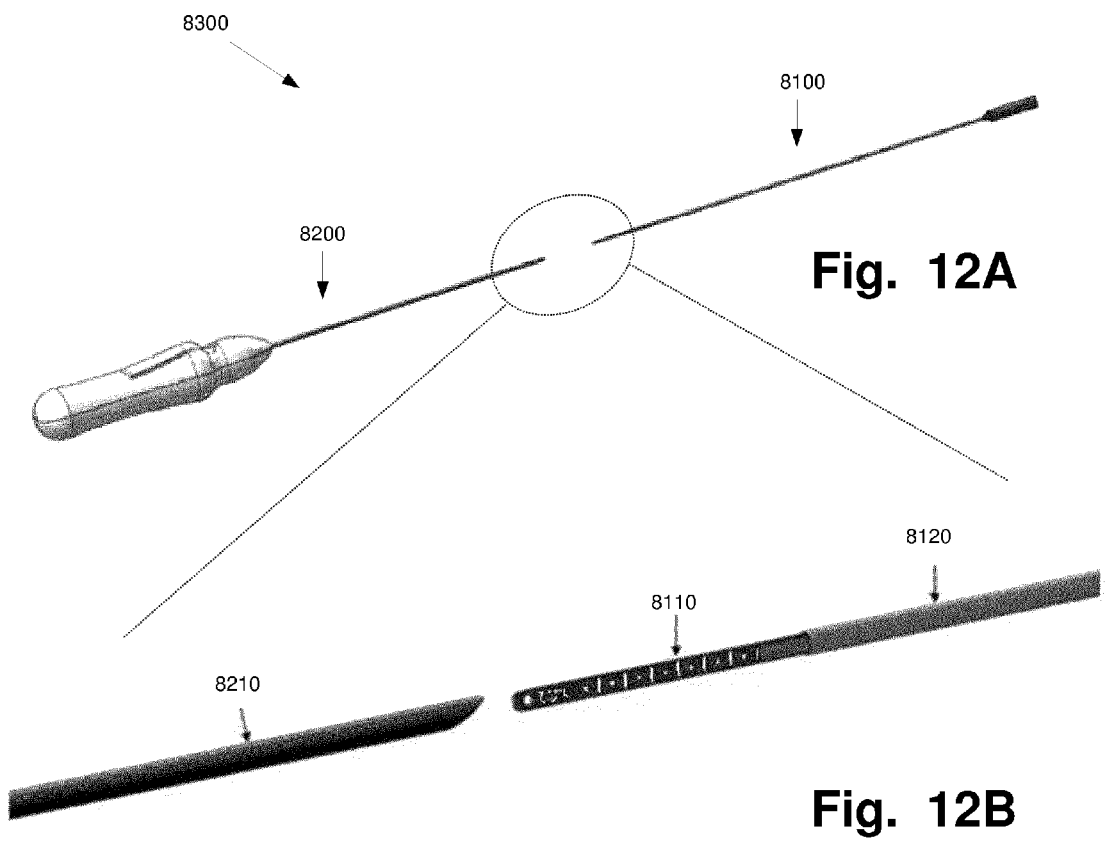
Fig. 12A
Fig. 12B

LAPAROSCOPE SYSTEM

CROSS-REFERENCE TO RELATED APPLICATIONS

This application is a national stage entry of PCT/EP2012/055041, filed on Mar. 21, 2012, which claims priority to U.S. Provisional Application No. 61/466,960, filed Mar. 24, 2011, each of the disclosures of which are hereby incorporated by reference in their entirety.

FIELD OF THE INVENTION

The present invention generally relates to endoscopy systems, and more specifically to micro-laparoscopy systems and methods of deployments thereof.

BACKGROUND OF THE INVENTION

Laparoscopic or minimally invasive surgery includes the use of several relatively small ports into the abdomen by which different types of instrumentation and accessories are introduced and used for different surgical interventions (usually performed under endoscopic vision). Although usually considered superior in several aspects to open surgery, the use of plurality of 5 to 15 mm ports still leads to local pain, scars, and possibly port related complications such as hernia in scars and the need for one or two assistants in addition to the surgeon. Laparoscopic methods and surgical device are described, for example, in U.S. Pat. Nos. 5,980,493, 7,593,777 and 7,316,699, the disclosures of which are fully incorporated herein by reference.

In a relatively new laparoscopic approach commonly referred to as "needlescopy", the laparoscopic ports are replaced with small incisions, usually between 2 to 3 mm in diameter. Narrow guide tubes are inserted into the small incisions and tiny surgical instruments are provided and manipulated through the tubes. The small instruments have very slender tips which make dissection and tissue maneuveration more difficult. Furthermore, the instrument tips may have a greater tendency to break and their removal may be cumbersome and difficult. The needlescopic surgery is performed under visualization made by a small television camera, replacing the traditional laparoscope which is substantially greater in size (commonly 5-10 mm in diameter) and contains illumination capabilities, that is introduced via a relatively large trocar unit, usually via the umbilicus. The small television camera, usually 3 mm or less in diameter, may be seen inferior considering its ability to capture and transfer high definition (HD) visual data, with respect to the traditional laparoscopes, due to its miniature size. A miniature camera is subjected to carry a smaller sized video sensor which inherently provides smaller resolution due to the decreased number of effective pixels. In order to achieve HD video resolution using approximately 5 µm pixels size the minimal active sensor surface should be about 8 mm the diameter, whereas in RGB format using approximately 2.5 µm pixels size, the minimal effective sensor area should be at least about 4 mm the diameter.

Due to the smaller effective size of the pixel, the amount or flux of the captured illumination may also be seen inferior, hence further affecting video quality. Currently, the needlescopic approach applies a plurality of thin optical fibers transferring illumination into the body cavity from external illumination source(s), due to excessive reduction of the transmitted light, as with respect to traditional laparoscopes built-in illumination.

A miniature camera may also be suffering from a smaller field-of-view (FOV), usually provided between 75° to 90° in standard laparoscopes, due to its use of a small diameter objective lens. Furthermore, a surgeon may also prefer a greater depth-of-field (DOF), which may be inherently compromised with a smaller lens, so that tissues and organs in background to the target location being in-focus will not be too blurred to identifying and monitoring.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a device, system, and a method, according to the appended patent claims.

In an aspect of the invention a visual device for laparoscopy is provided. The visual device is part of a visual system. The visual device includes an elongated connector for conducting a signal, such as a digital signal. The elongated connector has a distal end and a proximal end and is configured to be slidably arranged at least partially inside an insertion portion of a manipulation device. The insertion portion may be an elongated hollow needle. The vision device further includes a vision head member comprising an image pickup device and an illumination source. The visual head member is attached to the distal end of the elongated connector and the elongated connector is facilitating direct communication with an at least one contact element of the manipulation device.

In one embodiment of the visual device, the elongated connector is an elongated printed circuit board (PCB). The elongated connector may be at least 5 cm, optionally at least 10 cm, optionally at least 15 cm, optionally at least 20 cm, optionally between 15 cm to 35 cm, or higher, or lower or intermediate.

In one embodiment of the visual device, the proximal end of the elongated connector has a second contact element. The second contact element may comprise an image pickup contact and/or illumination contacts and/or power contact. This second contact element is connected to the first contact element of the manipulator.

In one embodiment of the visual device, the image pick up device comprises an image sensor and/or a lens. A lens may also mean a lens system including more than one lens element.

In one embodiment of the visual device, the image sensor may have an effective area size equal or larger than the outer diameter of the elongated connector. Further the lens may have a diameter equal or larger than the outer diameter of the elongated connector. The sensor is preferably configured to provide high definition image. The larger senor and/or lens provides for example improved field-of-view and depth of field capabilities.

In one embodiment of the visual device, the illumination source is a LED. The illumination source is provided directly at the vision head member to provide improved illumination capability. The LED may be white light LEDs or LEDs having narrow spectra around a preferred wavelength.

In one embodiment of the visual device, the illumination source is positioned at a distance from an objective opening of the image pick up device. When positioned from an objective opening, the vision head member may further comprising means for collecting, reflecting and/or projecting at least a portion of the light created by the illumination source towards a target.

In one embodiment of the visual device, the means for collecting, reflecting and/or projecting may be a reflector having a deployable formation.

In one embodiment of the visual device, the reflector is expandable and/or contractible between a smaller diameter to a greater diameter. This may for example be an iris design comprising a plurality of rigid or semi-rigid members.

In one embodiment of the visual device, the illumination source is coupled to a plurality of fiber optics provided over and along a length of the vision head member.

In one embodiment of the visual device, the plurality of optical fibers may be positioned over an expandable member thereby allowing projection of light in a cone-like form.

In one embodiment of the visual device, the elongated connector has a maximal outer diameter of 3 mm.

In one embodiment of the visual device, the elongated connector has an outer diameter of 0.1 to 0.3 mm smaller than an outer diameter of the insertion portion.

In one embodiment of the visual device, the image pickup device provides a field of view of 70° to 140°. The image pickup device may also be configured to provide a depth of field of 1 cm-30 cm.

In one embodiment of the visual device, the elongated connector is non-rigid.

In one embodiment of the visual device, the vision head member is substantially greater in diameter relative to a diameter of the insertion portion.

In one embodiment of the visual device, the vision head member is at least 5 mm in diameter.

A second aspect of the invention provides a manipulation device for laparoscopy. The manipulation device comprises an insertion portion having a distal end, a proximal end and a lumen. The lumen is extending axially at least partially a length of the insertion portion. The insertion portion is rigid. The insertion portion may be a hollow needle. When the insertion portion is housing an elongated connector, the insertion portion may provide a protection for and/or fortify the elongated connector.

The manipulator device further includes a handheld operation portion having a communication unit for communicating with an external device. The external device may be a power source, an electrical signal device, an image signal device, a video receiver, or others. The manipulation device also includes a contact element for facilitating direct communication to a vision head member of a visual device. The handheld operation portion is arranged at the proximal end of the insertion portion and an opening is arranged at the distal end of the insertion portion for slidably positioning an elongated connector of the visual device inside the lumen of the insertion portion.

In one embodiment of the manipulation device, the contact element is arranged inside said handheld operation portion.

In one embodiment of the manipulation device, the communication unit may be a cable or a contact for a cable. The communication unit may also additionally and/or alternatively provide wireless connection to an external device.

In one embodiment of the manipulation device, the insertion portion has an outer diameter of 0.5 to 3 mm. A sensor effective surface size and/or a lens diameter, any of which optionally provided in the vision head, may be greater than a maximal outer diameter of the manipulation device.

In one embodiment of the manipulation device, the lumen has an internal diameter smaller than an outer diameter of said insertion portion by 0.1 to 0.3 mm.

In one embodiment of the manipulation device, the insertion portions comprise a sharp distal end capable of piercing through bodily tissues.

In one embodiment of the manipulation device, the insertion portion provides support and rigidity to said elongated connector when it is housed therein.

In one embodiment of the manipulation device, the manipulation device is configured to be lengthened enough for manipulation of the vision head to any location/orientation in the cavity and be protruded out of the body via a distant airtight passage.

A further aspect of the invention provides a visual system for laparoscopy. The visual system comprises a visual device having a visual head member and an elongated connector; a manipulation device having a handheld operation portion, an insertion portion and a first contact element; and an external device comprising means to communicate with the vision head member, via the first contact element, when the elongated connector is mounted in a lumen of the insertion portion.

The insertion portion of the manipulation device is configured to be extendable out from a body cavity through an airtight passage whereby the elongated connector is configured to be slidably mounted into the lumen of the insertion portion outside of the body cavity upon the insertion portion is withdrawn into said body cavity.

A further aspect of the invention provides a method of assembling a visual system comprising a manipulation device having an insertion portion and a first contact element and is connectable with a visual device having a vision head member. The method of assembling comprising extending the distal end of the insertion portion out of a cavity through an airtight passage. The airtight passage is extending from inside the body cavity to outside the body cavity. The airtight passage comprising an internal diameter greater than a maximal diameter of the vision head member. The method further comprising connecting the visual device to the manipulation device and withdrawing the visual device into the cavity through the airtight passage.

In one embodiment of the method, the visual device is a rigid laparoscope or a laparoscopic camera.

In one embodiment of the method, the vision head member comprises at least one of lens, visual signal conductor, digital signal conductor, printed circuit board (PCB).

In one embodiment of the method, the insertion portion has a maximal diameter equal or smaller than 3 mm.

In one embodiment of the method, the vision head member comprises at least one of lens, image sensor and illumination source.

In one embodiment of the method, further comprising, passing telescopically an airtight sleeve into the cavity through the airtight passage until adjacent the insertion portion's distal end, the sleeve comprising a minimal inner diameter equal or greater than a maximal diameter of the vision head member.

In one embodiment of the method, the extension of said insertion portion's distal end is through the airtight sleeve.

In one embodiment of the method, the vision head member is provided connected to an elongated connector slidably mountable into a lumen of the insertion portion and comprising at least one PCB, and/or at least one second contact element disposed on a proximal end thereof.

In one embodiment of the method, the visual system further comprising a control unit and/or a display device connectable to the insertion portion.

In one embodiment of the method, the connection of the visual device to the manipulation device comprising slidably mounting a proximal end of the elongated connector into a lumen of the insertion portion and connecting the control unit and/or display device to the insertion portion and/or visual device to facilitate direct communication with the at least one second contact element.

One aspect of the invention provides for an alternative manipulation device for laparoscopy. The manipulation device comprises an elongated connector for conducting a signal. The manipulation device has a distal end and a proximal end. Further the manipulation device includes a handheld operation portion having a communication unit for communicating with an external device and a contact element for direct connecting to a vision head. The handheld operation portion is arranged at the proximal end of the insertion portion and at the distal end of the insertion portion the vision head member is detachable.

Additionally the manipulator may include an additional rigid insertion portion housing the elongated connector for supporting the elongated connector.

One aspect of the invention provides for an alternative visual system that has a proximal end and a distal end. The visual system comprises a handheld operation portion arranged at the proximal end of the visual system and a vision head member arrange at said distal end of said visual system. The system further includes an elongated connector configured for conducting a digital signal between the vision head member and the handheld operation portion. The system also includes an external device comprising means to communicate with the vision head member, via a first contact element arranged in the visual system.

The visual system is mountable by extending a distal end of the visual system out from a body cavity through an airtight passage, whereby the visual head member is detached to the first contact element at a distal end of the elongated connector. Alternatively, the elongated connecter is pre-connected to the vision head member and a proximal end of the elongated connector is slidably connected to the first contact element arranged apposition the handheld operation portion.

In both cases, upon connection, a direct communication is facilitated between the visual head member and the external device, whereafter the vision head member is withdrawn into the cavity through the airtight passage.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 2 schematically illustrates a first exemplary visual system, in accordance with embodiments of the invention;

FIGS. 3A-C schematically illustrate perspective and cut views of an exemplary laparoscopic insert unit, in accordance with embodiments of the invention;

FIGS. 4A-D illustrate different deployment stages of the exemplary visual system of FIG. 2, in accordance with embodiments of the invention;

FIG. 5 schematically illustrates a second exemplary visual system, in accordance with embodiments of the invention;

FIG. 6 schematically illustrates a third exemplary visual system, in accordance with embodiments of the invention;

FIG. 7 schematically illustrates a fourth exemplary visual system, in accordance with embodiments of the invention;

FIG. 11 is illustrating an exemplary embodiment of a manipulation device; and

FIG. 12 A-B are illustrating an exemplary embodiment of a system before visual device is slidably connected to the manipulation device.

DETAILED DESCRIPTIONS OF EXEMPLARY EMBODIMENTS

Figure 1A:
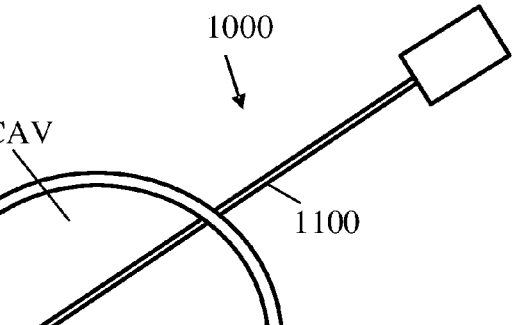
FIGS. 1A-D illustrate different deployment stages of a schematically illustrated conceptual visual system, in accordance with embodiments of the invention.

It is understood that the terminology used herein is used for the purpose of describing particular embodiments only, and is not intended to limit the scope of the invention. It also is be noted that as used herein and in the appended claims, the singular forms "a," "an," and "the" include the plural reference unless the context clearly dictates otherwise. Thus, for example, a reference to "a lens" is a reference to one or more lenses and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals reference similar parts throughout the several views of the drawings.

In some instances, preferred embodiments may be described in the context of exemplary laparoscopic imaging systems for ease of description and understanding. However, the invention is not limited to the specifically described devices and systems, and may be adapted to various applications without departing from the overall scope of the invention.

In an aspect of some embodiments of the present invention, there is provided a laparoscopic system capable of acquiring images in a patient's body cavity during laparoscopic surgeries, the laparoscopic system includes a microlaparoscopic sized elongated body, usually 3 mm or less in diameter, detachably connectable to a regular sized laparoscopic insert unit or camera head. The slender body and regular sized camera head are connectable within the body cavity after first penetrating therein with the slender body at a chosen entry point, leaving a minimal penetration/incision mark and avoiding potential complications and/or hazards associated with regular sized trocar entries as in classical laparoscopic surgeries. Due to its small diameter, the elongated body can be introduced at more possible entry points across the anterior abdominal wall, that otherwise, such as in classic laparoscopic surgeries, would have been avoided mainly due to clinical and cosmetic considerations. Although in laparoscopic surgeries the laparoscope is introduced via a large trocar usually through an incision at the umbilicus, it is advantageous to position a laparoscopic system at different positions. For example, in gallbladder removal surgeries it may be advantageous to position the camera head at the left upper quadrant of the abdominal cavity, whereas in colon surgeries it may be advantageous to position the camera head close to the dissection in the upper abdomen. Other than the advantage of creating a small sized, optionally scarless entry, such a displaced laparoscope positioning vacates the main umbilicus trocar for inserting large sized instruments into the body cavity, such as suction, clippers, and staplers.

Optionally, two or more camera heads are introduced and assembled in a body cavity at different positions and/or orientations, optionally at least one camera head is deployed in addition to a regular laparoscope deployed in the main trocar. The use of two or more camera heads and/or laparoscopes, provided a few centimeters distant one from the other, may be beneficiary to obtain high quality 3D images. In some embodiments, at least two camera heads are deployed at a distance of 7 cm or more, known as the minimal focal length of the human eye.

The present invention, in some embodiments thereof, relates to a laparoscopic system configured for assembly, optionally in and/or by traveling through a body cavity, where it should be then activated for monitoring a surgical procedure. After ending of the surgical procedure, the system may then be disassembled in/through the body cavity and its parts may be removed. In some embodiments, the system includes at least two parts differentiated by dimensions and/or shape that are delivered into the body cavity through different openings of the cavity, optionally surgically created openings, either by pre-made incisions or by actual front tip penetrations. In some embodiments, the laparoscopic system includes a slender elongated body detachably connectable to a regular sized camera head. In some embodiments, a first part or member of the laparoscopic system (e.g., the elongated body) is introduced into the cavity at an entry point, then projected out of the cavity and/or out of patient body at a second point, then attached with a second part or member (e.g., the camera head) and withdrawn back into the cavity. In some embodiments, the system parts delivery and/or assembly is monitored using a second visual system and/or by an optional camera head of the laparoscopic system. The same camera head may be first introduced into patient's body cavity through a main port (e.g, at umbilicus positioned port/trocar) to assist in choosing an entry point for the camera head elongated body and to monitor its penetration and entry; and then be connected to the elongated body by first being pulled back from the body cavity and connected (in reversed position) at its back side, for example outside patient's body.

In some embodiments, the system includes a thin member that is entered through a first smaller opening (optionally, 3 mm or less in diameter) and a second wider member that is entered through a second greater opening (optionally, 5 mm or more in diameter). In some embodiments the laparoscopic system comprises an elongated hollow needle having an external diameter equal or less than 3 mm that is optionally configured for penetrating into the body cavity while passing tissue layers, such as skin tissue and/or connective tissues. In some embodiments, the hollow needle is rigid or semi-rigid.

In some embodiments, the laparoscopic system further includes a camera head which comprises at least one of: an image sensor, a lens, and an illumination source. In embodiments of the invention, the camera head is sized to include at least one medium or large image sensor, optionally an HD image sensor, having pixel size of at least 2.5 µm the pixel, optionally at least 4 µm the pixel. The camera may allow high definition recording or real-time projecting on large screen or TV with a chosen DOF and contrast, thereby allowing high quality monitoring of the surgical procedure by the practicing team. In some embodiments, the camera head is 5 mm or more in diameter, optionally between 8 to 10 mm, or higher. In some embodiments, the camera head includes a lens (e.g., an objective, optionally in combination with more optical elements), optionally allowing a field-of-view of about 75° or more, optionally 90° or more, or higher, or lower, or intermediate. In some embodiments the DOF is chosen to cover the abdomen cavity. Preferably the DOF may be 1 cm-30 cm. In some embodiments of the invention, the camera head further includes at least one illumination source, optionally a plurality of illumination sources, optionally LED type.

In some embodiments, the camera head is capable of acquiring and/or recording at least one of: visual images, ultrasound and/or infrared images (for example, in order to observe tumors or lumps in tissues, or to observe blood vessels), optical coherent tomography image, marked antibodies images, or others.

In some exemplary embodiments of the invention, the camera head is provided connected, optionally at its back end, to an elongated connector having at least one contact disposed at a free end thereof. The elongated connector may be designed to directly electrically connect between the camera head, positional at any chosen point in the body cavity and/or remotely from body cavity wall, and a power source provided outside patient's body. The elongated connector may be equipped to also connect at least one illumination source provided with/in the camera head with the external power source. Optionally, the elongated connector is slidably mountable in the hollow needle. In some embodiments, the elongated connector, once mounted in the hollow needle, facilitates connectability with an external device such as a power source, an electrical signal device, an image signal device, a video receiver, or others. Alternatively or additionally, the camera head may or may not include a mountable elongated connector, but is wire or wirelessly connectable to an outside source or receiver.

In some embodiments, the system further includes and/or is connectable with a camera control unit and/or a display device which comprises means to communicate with the at least one contact when the elongated connector is mounted in said needle.

The present invention, in some embodiments thereof, also relates to a method of assembling and/or deploying a visual device which comprises a slender elongated body connectable with a wide visual head, in a sealed perforatable cavity, optionally a body cavity, the method comprising: passing a distal end of the elongated body into the cavity through a first miniature perforation; providing an airtight passage extending through a second perforation, the airtight passage comprising an internal diameter greater than a maximal diameter of the visual head; extending the elongated body distal end out of the cavity through the airtight passage; connecting the visual head to the elongated body; and withdrawing the visual device into the cavity.

In some embodiments, the visual head is provided connected to an elongated connector which is slidably mountable to a passage, optionally a lumen, of the elongated body and comprising at least one PCB, and/or at least one contact disposed on a free end thereof. In some embodiments, the visual device further comprises a control unit and/or a display device connectable to the elongated body and/or visual head.

Optionally, connecting the visual head to the elongated body comprises the following steps: slidably mounting the free end of the elongated connector in the elongated body passage; and connecting the control unit and/or display device to the elongated body and/or visual head to facilitate direct communication with the at least one contact.

Referring now to the drawings, FIGS. 1A-D illustrate different deployment stages of a conceptual visual system 1000, in accordance with embodiments of the invention. System 1000 is deployed prior to utilization in a body cavity, for example in abdominal cavity CAV. System 1000 may include any endoscopic or laparoscopic related visual device, for example a rigid lens-bar type endoscope, that may be connectable to a video recording camera located outside the body; or alternatively, to an intrusive camera unit adapted to record video images from within CAV.

System 1000 includes a slender body 1100 which incorporates means for image pickup and/or transfer from an image source (e.g., an illuminated internal organ) located in body cavity CAV to an image receiver located outside the body (not shown) which may be a human eye, a solid-state sensor, a camera, a video display device, or others. In some embodiments, slender body 1100 is particularly thin in relation to dimensions of currently known laparoscopes in order to produce minimal harm to bodily tissues when penetrating and/or operating through a port or an incision in tissues surrounding CAV. Slender body 1100 may include a maximal diameter equal or less than 5 mm, optionally equal or less than 3 mm, optionally equal or less than 1.5 mm, or higher or lower or intermediate values.

In some embodiments, system 1000 is fully operable only when coupled with head 1200 that is detachably connectable to a distal tip of slender body 1100. Head 1200 may include any function or element necessary for the proper and/or requested operation of system 1000, for example a camera, a lens, an illumination source or any combination thereof. In some embodiments, it is necessary to introduce a system part, such as system head 1200, which incorporates a dimension that is substantially greater than a correlated dimension of slender body 1100. In some exemplary embodiments, system head 1200 includes a minimal diameter that is equal or greater than 3 mm, optionally equal or greater than 5 mm, optionally equal or greater than 10 mm, or higher or lower, or intermediate value. In some embodiments, head 1200 is configured to be transferable through a regularly sized laparoscopic trocar unit, such as trocar 100 (shown in FIG. 1C), having minimal internal diameter that is equal or greater than 5 mm, optionally equal or greater than 10 mm.

Figure 1B:
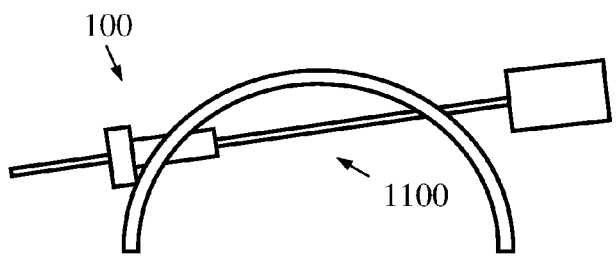
Figure 1C:
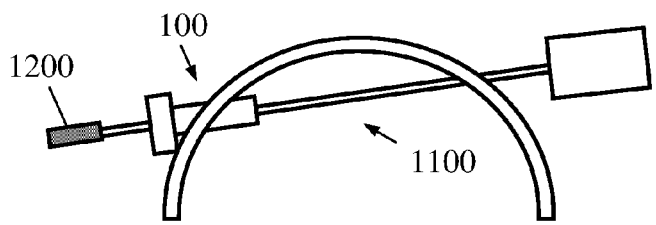
Figure 1D:
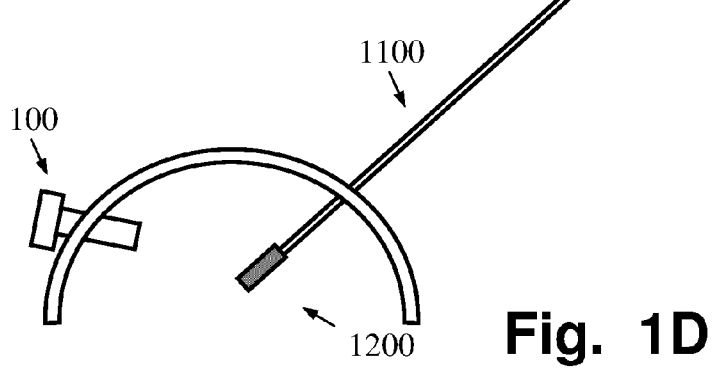

In FIG. 1A, system slender body 1100 is positioned after insertion into abdominal cavity CAV and prior to attaching of system head 1200. Optionally, trocar 100 may be housing a second visual unit such as an endoscope (not shown), which can be operated for monitoring at least part of the surgical procedure, or only deployment stages of visual system 1000 in CAV. In order to attach head 1200 to distal end of slender body 1100, the surgeon needs to pass slender body 1100 through the lumen of trocar 100 from CAV to an outer body environment (as shown in FIG. 1B) optionally by aiming towards the endoscope lens (or "towards his eye"). Before or during body 1100 travel through lumen of trocar 100, the endoscope is withdrawn. Next, as shown in FIG. 1C, head 1200 is connected, optionally manually, to body 1100. Then, the complete visual system 1000 is pulled back into abdominal cavity CAV and the surgical procedure may begin. Alternatively, instead of an endoscope, system head 1200 may be used to monitor and assist in choosing point-of-entry and slender body 1100 and/or traveling to and through trocar 100 to be connected thereto outside patient's body.

In some embodiments, trocar 100 includes an air-tight two-way valve or other air-sealing mechanism (not shown) that can allow traveling of instrumentation therethrough in both directions totally or significantly without derived loss of air/gas (usually but not necessarily—$CO_2$) previously introduced to abdominal cavity CAV. Trocar 100 may be of any preferred size, and usually between 3 to 20 mm in diameter, optionally about 10 mm or 12 mm (e.g., similar in size to regular laparoscopic port). Trocar 100 may be sized (e.g., smallest cross section) to accommodate a largest of a surgical tool in a specific tool kit.

In some embodiments, slender body 1100 includes a distal tip. Slender body 1100 tip is optionally sharp and/or chamfered in order to allow at least one of tissue penetration and easier engagement with head 1200. Optionally, the tip is a Veres needle allowing penetration through skin and abdominal wall tissue while preventing injury of internal organs (e.g., bowels) when not "armed". Optionally, slender body 1100 includes interlocking means at its distal portion, e.g., threading or a groove for snap-locking (not shown), for firmly connecting with head 1200, or alternatively by any means of friction, pressure or other means known to art.

At least part of the instruments are made from rigid or semi-rigid biocompatible materials as known to a person skilled in the art, and may include stainless steel, optionally hardened or reinforced by carbon coating or fibers, ceramic materials, plastic/polymeric materials (e.g., PEEK), composite materials (e.g., carbon-epoxy), or any combination thereof.

Reference is now made to FIG. 2 which schematically illustrates a first exemplary visual system 2000, in accordance with embodiments of the invention. In some embodiments, system 2000 mainly comprises of a manipulation part 2100, which is similar in at least some aspects to previously presented slender body 1100; a laparoscopic insert unit 2200 which is detachably connectable with manipulation part 2100; and an external visual unit 2300 that is connectable with manipulation part 2100 and/or with laparoscopic insert unit 2200 with at least one wired or wireless connection, such as image pickup cable 2130.

In some embodiments, manipulation part 2100 comprises an insertion portion 2110 having length and outer diameter, optionally rigid or semi-rigid, which facilitate manual manipulation inside a body cavity, optionally allowing advancement to and/or orientation at any location in the relevant body cavity. The insertion portion 2110 is connected to a handheld operation portion 2120. In some embodiments, insertion portion 2110 includes a sharp and/or a chamfered distal tip. Alternatively or additionally, insertion portion 2110 is configured for passing through a laparoscopic trocar. In some embodiments, insertion portion 2110 is configured for enclosing and/or facilitating strength to an image pickup device attachable thereto. In some embodiments, insertion portion 2110 includes an inner lumen having a minimal diameter and an opening at its distal end allowing insertion and enclosing of longitudinal inserts having maximal outer diameter equal or smaller than the inner lumen minimal diameter.

In some embodiments, insertion portion 2110 largest cross section may be 0.5 to 5 mm in diameter, optionally 1 to 2.5 mm, optionally about 1 mm, about 1.5 mm or about 2 mm or higher or lower or intermediate. In some embodiments, insertion portion 2110 includes a lumen having an internal diameter smaller than its outer diameter by 0.1 to 0.3 mm. For example, insertion portion 2110 may include an outer diameter of 2.2 mm and internal diameter of 2.05 mm. Insertion portion 2110 length may be between 15 to 50 cm, and optionally, a kit may include several length per patient size, for example a 20 cm length for a baby, a 27 cm length for moderate size adult and 45 cm length for heavy sized adult.

In some embodiments, laparoscopic insert unit 2200 is a rigid lens bar type laparoscope. Alternatively, laparoscopic insert unit 2200 is a video camera type laparoscope, optionally including a digital video camera. In some embodiments, laparoscopic insert unit 2200 includes an image pickup device 2210 connected (optionally, detachably connectable) to an elongated connector 2220. In some embodiments, image pickup device 2210 includes at least one solid state sensor, such as CCD (charge coupled device) or CMOS (complementary metal oxide semiconductor), and optionally further includes at least one lens and/or other optical element, and/or at least one illumination source or projector, such as LED (light-emitted diode) illuminator. Elongated connector 2220 allows video and/or image signal and/or digital signal and/or electrical current and/or illumination transfer in at least one direction along its length. In some embodiments, elongated connector includes at least one PCB (printed circuit board) and/or optical fiber and/or communication cable. Optionally, elongated connector 2220 is non-rigid and gains mechanical endurance/strength when enclosed in insertion portion 2110. In some embodiments, elongated connector 2220 includes electrical conductive contacts in at least one end. In some embodiments, elongated connector 2220 includes a covering or sleeve (not shown) having internal or outer diameter between 0.5 to 2.5 mm, for example 1.8 mm in ID and 2 mm in OD where it should enclose at least one elongated PCB and be mountable in a insertion portion 2110 having ID equal or slightly greater than 2 mm.

In some embodiments, laparoscopic insert unit 2200 is connectable to an external visual unit 2300 when properly installed within manipulation part 2100, optionally by image pickup cable 2130, thereby allowing control, display, recording and/or other functions from outside patient's body. External visual unit 2300 includes in some embodiments a CCU (camera control unit) 2310 and a display device 2320, optionally interconnectable with a communication cable 2330. In some embodiments, CCU 2310 includes a signal processing device with an image processing circuit. CCU 2310 may be configured to generate a video signal based on transmitted image signals and to output the video signal to display device 2320.

Reference is now made to FIGS. 3A-C which schematically illustrate perspective and cut views of an exemplary laparoscopic insert unit 3000, in accordance with embodiments of the invention. As shown in FIG. 3A, laparoscopic insert unit 3000, similarly to previously described unit 2200, includes an exemplary image pickup device or camera head 3100 and an exemplary connector unit 3200. In embodiments, and as shown in FIG. 3B, which schematically illustrates a transverse cut view of a distal portion of laparoscopic insert unit 3000, exemplary camera head 3100 includes a housing 3110, a lens 3120 with at least one optical element, at least one LED 3130 (in this example, two LEDs) and an image sensor circuit 3140 (including, optionally, at least one CCD or CMOS sensors). In some embodiments, lens 3120 allows an angle or a field of view between 70° to 140°, optionally 90° to 110°, whereas in a provided kit, different heads and/or lens couplings may be provided which are differentiated by angle of view. In some embodiments, camera head 3100 includes a distance of view between 0.1 and 40 cm, optionally 1 to 20 cm. In some embodiments, camera head 3100 further includes cooling means, passive or active, for LEDs 3130 (not shown).

In embodiments, and as shown in FIG. 3C, which schematically illustrates a cross section cut view of connector unit 3200, and in FIGS. 3A and 3C, connector unit 3200 includes a sleeve 3210 enclosing longitudinal PCBs, in this example a single image pickup PCB 3220 and two LEDs PCBs 3230. Alternatively, at least one of the PCBs is substantially shorter whereas other means (such as wires) are used to transmit signals across connector unit 3200 length. Image pickup PCB 3220 is configured to transfer power and/or image signal and/or digital content from circuit 3140 to an external CCU (not shown) and/or power source and/or vice versa, when properly in contact with sensor-PCB contacts 3150 and image pickup contacts 3240. Optionally, at least ten sensor-PCB contacts 3150 are used, for example 14 contacts. LEDs PCBs 3230 are configured to transfer power to LEDs 3130 from an external power source (not shown), when properly in contact with LEDs-PCB contact(s) 3160 and LEDs-power contact(s) 3250. Alternatively, instead of LEDs PCBs 3230 and contacts 3160, a power line is connected (e.g., soldered) to LEDs 3130 and passed over and along image pickup PCB 3220 until its proximal end where optionally it is connected with short PCB connectors. In a third alternative, camera head 3100 includes a power source (not shown) for powering the LEDs 3130 and/or circuit 3140.

In some embodiments, LEDs 3130 project illumination towards a target object in a body cavity which is then reflected back and picked up by circuit 3140 through lens 3120 and captured as a digital image. Digital images are then transmitted to an external CCU (not shown) located outside the body cavity via image pickup PCB 3220.

Reference is now made to FIGS. 4A-D which illustrate different deployment stages of the exemplary visual system 2000, previously shown in FIG. 2, in body cavity CAV (optionally previously inflated), in accordance with embodiments of the invention. In some embodiments, manipulation part 2100 of system 2000 is slightly introduced into CAV in order to avoid any unnecessary harm to internal organs. Manipulation part 2100 may penetrate into CAV through tissue layers or inserted through a previously performed incision or a dedicated trocar (not shown). Laparoscopic trocar 2400 is also introduced into CAV, optionally through the umbilicus. In some embodiments, trocar 2400 is configured to allow bi-directional travel therethrough from inside-out and from outside-in with minimal to no leak of inflating gas entrapped in CAV. Trocar 2400 includes or configured to allow passage of an internal telescopic sleeve 2450 which can be extended, oriented and manipulated to a plurality of locations in CAV. A laparoscope 2500 is inserted through trocar 2400 to allow visual for deploying visual system 2000. Laparoscope 2500 may be any type laparoscope, and optionally may include the laparoscopic insert unit 2200 that is intended for later deployment with the other parts of system 2000.

As shown in FIG. 4A, laparoscope 2500 is used to scan CAV periphery for manipulation part 2100 distal tip. In FIG. 4B, telescopic sleeve 2450, optionally with laparoscope 2500 enclosed within, is then extended towards until adjacent or contacting the protruding distal tip of manipulation part 2100. Alternatively, telescopic sleeve 2450 is extended towards a chosen point on CAV periphery and pushes it outwardly thereby visually signaling an entry point for manipulation part 2100, to which it can penetrate.

Inner diameter (e.g., lumen diameter) of telescopic sleeve 2450 may be about 3 to 15 mm, or optionally about 10 mm; and its outer diameter may be about 4 to 20 mm. In some embodiments, additionally or alternatively to using telescopic sleeve 2450, other locating and/or guiding and/or grasping/connecting devices (not shown) may be used to locate and/or guide and/or grasp distal end of manipulation part 2100 in CAV and assist or use in transferring it through trocar 2400 to outer body environment.

Once in direct contact, manipulation part 2100 can be pushed into and through telescopic sleeve 2450 until projecting outside CAV and patient's body, as shown in FIG. 4C. While pushing manipulation part 2100, or before introduction into telescopic sleeve 2450, laparoscope 2500 is withdrawn. Next, laparoscopic inset unit 2200 is introduced into manipulation part 2100 to assemble visual system 2000. A shown in FIG. 4D, system 2000 may then be pulled back into CAV and allowing an optional use of trocar 2400 for passage of elements therethrough and following surgical intervention under visual surveillance.

Reference is now made to FIG. 5 which schematically illustrates a second exemplary visual system 4000, in accordance with embodiments of the invention. System 4000 includes a manipulation part 4100 comprising a rigid elongated connector 4110, a handheld operation portion 4120 and an image pickup cable 4130 connectable to an external visual unit (not shown). System 4000 further includes a camera head 4200 detachably connectable to elongated connector 4110. In some embodiments, camera head 4200 is substantially greater in diameter relative to diameter of elongated connector 4110. In some embodiments, camera head 4200 is similar in design and/or operation to previously presented camera head 3100 although it may differ in its connection type and means with the elongated connector. Installment and/or operation of system 4000 may be similar to those of system 2000.

Alternatively, the elongated connector 4110 may be housed in a insertion portion for protection and/or increasing the rigidity.

Reference is now made to FIG. 6 which schematically illustrates a third exemplary visual system 5000, in accordance with embodiments of the invention. System 5000 is a rigid rod lens type laparoscope which includes a thin rigid laparoscope unit 5100 comprising a rigid insertion portion 5110 optionally enclosing an image guide (e.g., including optic carrier and lenses); a handheld operation portion 5120 optionally detachably connected to a video camera 5140; and an image pickup cable 5130 connectable to an external visual unit (not shown). System 5000 further includes a detachably connectable illumination sleeve 5200 having a substantially greater diameter in relation with the thin rigid laparoscope unit 5100. In some embodiments, illumination sleeve 5200 includes an internal lumen or bore having a diameter substantially similar to external diameter of a distal portion of insertion portion 5110, and is configured to be deployed thereupon. In some embodiments, illumination sleeve 5200 is self powered or powered by an external power source connectable via rigid insertion portion 5110. Installment and/or operation of system 5000 may be similar to those of system 2000.

Reference is now made to FIG. 7 which schematically illustrates a fourth exemplary visual system 6000, in accordance with embodiments of the invention. Similarly to system 5000, system 6000 is also a rigid rod-lens type laparoscope, that includes a slender rigid laparoscope unit 6100 comprising a rigid insertion portion 6110 optionally enclosing a bundle of image guide and light guide (not shown); a handheld operation portion 6120 optionally detachably connected to a video camera 6150; an image pickup cable 6130 connectable to an external visual system (not shown); and an illumination cable 6140 connectable to an external illumination source (not shown). System 6000 further includes a detachably connectable distal rod lens 6200 having a substantially greater diameter in relation with the thin laparoscope unit 6100. In some embodiments, distal rod lens 6200 allows greater view angle than can be achieved in smaller diameters rod lenses such as those enclosed in insertion portion 6110. Installment and/or operation of system 6000 may be similar to those of system 2000.

In some embodiments of the present invention, a laparoscopic insert unit and/or a camera head may include at least one illumination source provided as an integral part or as a potential add-on component. In some embodiments, it may be preferable to project much more light to a target object, for example in order to improve visualization and/or video quality parameters, so that larger illumination sources (e.g., LEDs), and/or in larger numbers, may be delivered with the laparoscopic insert unit. Optionally, alternatively or additionally, a need may arise to decrease/minimize to heat created by the illumination source(s) next to the lens/objective and/or any temperature-sensitive component. Optionally, alternatively or additionally, a need may arise to decrease/minimize the diameter of the unit and, for example, make it only slightly larger than the cased lens/objective.

In some embodiments of the invention, according to any of the above considerations, and/or to any other consideration, there may be provided a laparoscopic insert unit (or a camera head) comprising illumination source(s) located away from, optionally remotely behind, the lens/objective opening. In some variations of these embodiments, means may be provided to collect, reflect and/or project most or all light created in the illumination source(s) towards a certain target, optionally in-front and/or radially away from the object/lens.

Figure 8:
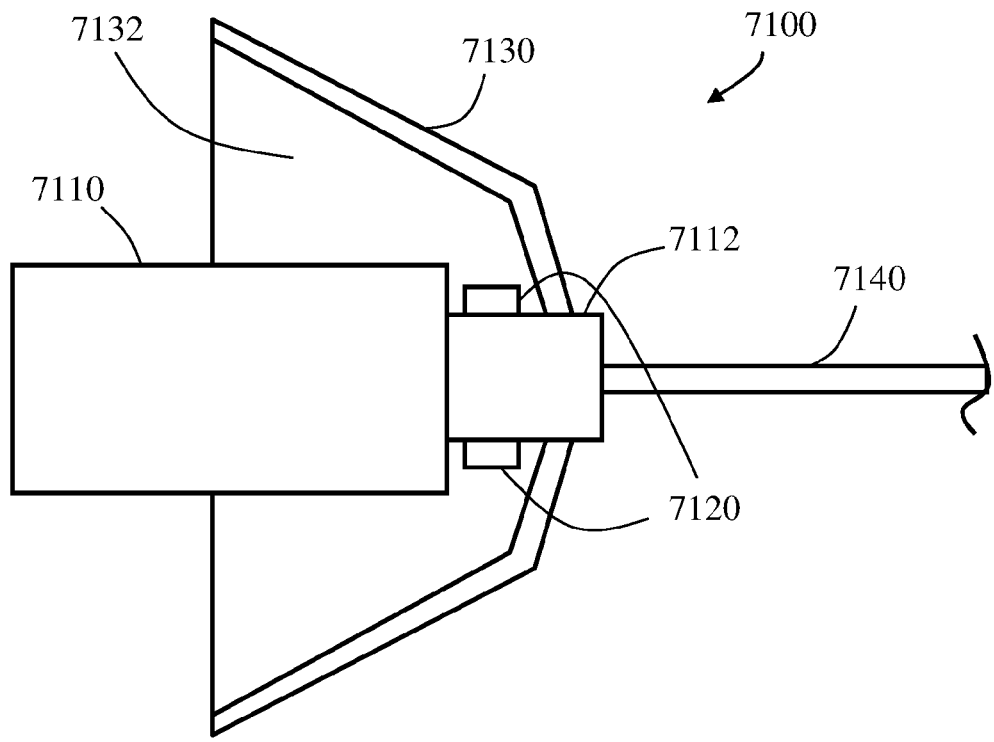
FIG. 8 schematically illustrates a partial cut view of an exemplary laparoscopic insert unit comprising an illumination reflector, in accordance with embodiments of the invention.

Reference is now made to FIG. 8 which schematically illustrates a partial cut view of an exemplary laparoscopic insert unit 7100 which comprises an illumination reflector 7130 (shown in transverse cut view), in accordance with embodiments of the invention. Laparoscopic insert unit 7100 includes a wide video camera head body 7110 (shown in a non-cut side view), which may encase lens/objective, image sensor and electronics (not shown), that is provided connected with an elongated slender connector unit 7140 (shown in part). Camera head body 7110 may end with a smaller diameter portion 7112 that is connected or enclosing a proximal end of connector unit 7140. A plurality of illumination sources (although one may suffice) 7120 are provided on outer periphery of smaller portion 7112 and optionally, though not necessarily, do not emerge over body 7110 largest diameter. The illumination sources may be set to point radially outward, in a reversed direction (towards connector unit 7140) or in any angled fashion. In an exemplary embodiment, the illumination sources are LED sources electrically connectable to a power source provided outside a patient's body (not shown) via connector unit 7140 and along its length. In some embodiments, reflector 7130 is designed and shaped, at a deployed formation, to reflect most of the light created by illumination sources 7120. In some embodiments, reflector 7130 includes an inner surface 7132 made or coated with a reflecting material as known to art. Reflector 7130 may be shaped to collect and/or focus scattered light originating from the plurality of illumination sources 7120 towards a chosen target area. Reflector 7130 may be rigid, semi-rigid or elastic; it may be formed of or assembled to a single piece or comprise a plurality of components (e.g., an iris design comprising a plurality of rigid or semi-rigid members; not shown). In some embodiments, reflector 7130 is expandable and/or contractible between a smaller diameter to a greater diameter. The exemplary smaller diameter may be smaller, substantially the same or slightly greater than diameter of camera head body 7110 so that it may maintain a thinner introductory size and later expand, either selectively or predeterminedly, automatically or per demand, when in position inside a patient's body cavity.

Figure 9:
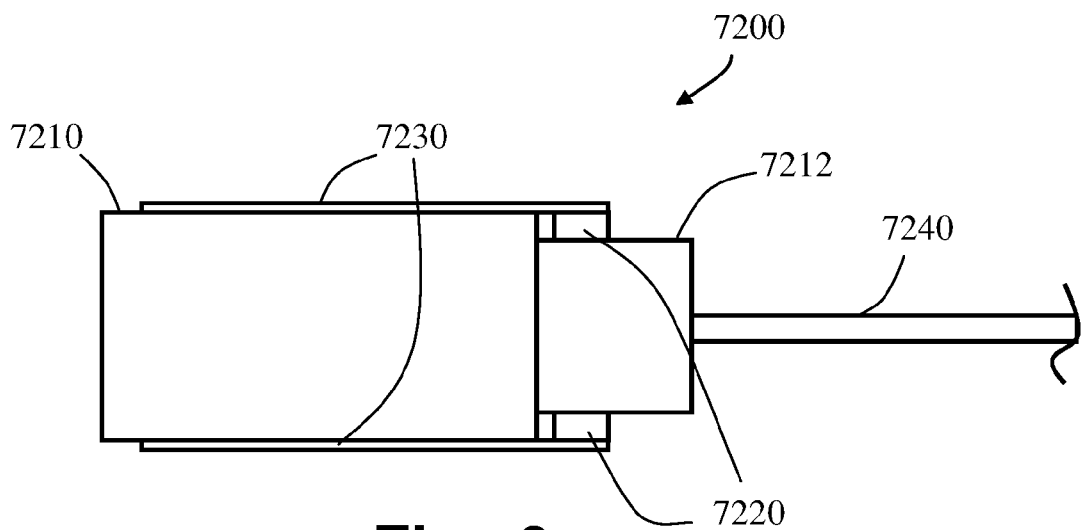
FIG. 9 schematically illustrates a partial cut view of an exemplary laparoscopic insert unit comprising illumination fiber optics, in accordance with embodiments of the invention.

FIG. 9 schematically illustrates a partial cut view of another exemplary laparoscopic insert unit 7200 comprising illumination fiber optics 7230, in accordance with embodiments of the invention. Similarly to unit 7100, laparoscopic insert unit 7200 includes a wide camera head body 7210 incorporating a smaller sized distal portion 7212 and connected to a slender elongated connector unit 7240. A plurality of illumination sources 7220 are also similarly positioned over smaller portion 7212 periphery. Instead of reflecting means, the plurality of fiber optics 7230 may be provided over and along a length of camera head body 7210, thereby allowing travel of light from illumination sources 7220 distally and towards and in front of camera head body 7210. A plurality of optical fibers may be used to transfer light from a single illumination source. Optical fibers may be positioned over an expandable member (not shown) thereby allowing projection of light in a cone-like form.

Figure 10A:
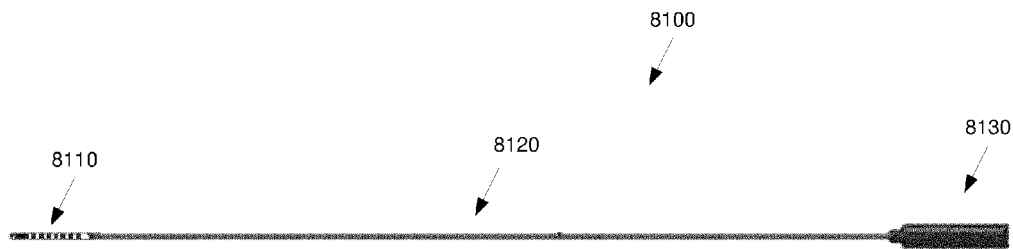
FIG. 10 A-B are illustrating an exemplary embodiment of a visual device having an elongated connector a vision head member at one end and a male connector at the other end.

FIGS. 10A and B illustrate an exemplary one unit camera and male connector 8100 embodiment of a self-illuminating visual head 8130 connected to an elongated internal shaft 8120 being an elongated connector having a male connector 8110. The visual head 8130 has a camera unit 8140 and to illuminating LEDs 8150. The male connector 8110 is in this embodiment a non-optical connector, such as electrical conductive, for powering, controlling and transmitting information. The use of a non-optical connector enables a small cross-section of the elongated internal shaft 8120 and may therefore be advantageous to be used for scarless laparoscopi procedures.

FIG. 11 illustrates an exemplary manipulation part 8200 where a rigid insertion portion is an outer shaft 8210, such as a needle. The rigid insertion portion is configured to provide a rigid support for the elongated connector. The manipulator part 8200 further comprises, a handheld operation portion, such as a handle 8220. Inside the handle 8220 is a female connector 8230 located to be connected to the male connector 8110 of the camera and male connector 8100. Further, the handle 8200 has a video console cable connector 8240 for connecting the visual head 8130 with an external visual unit, such as a screen. Alternatively, instead of a video console cable connector 8240, the handle 8220 may be equipped with a wireless communication unit for transferring the signal to the external visual unit.

FIGS. 12 A and B illustrates an exemplary assembly 8300 of a camera and male connector 8100 and a manipulation part 8200. The internal shaft 8210 with the male connector 8110 is pushed into the outer shaft, such as a needle, 8210 until the male connector 8110 connects with the female connector 8230 inside the handle 8220. When connected, most of the internal shaft 8120 is housed inside the outer shaft 8210. The mounting of the assembly 8300 is conducted by having the outer shaft 8210 extending out of the body cavity through an airtight passage as previously described herein.

Figure 10B:
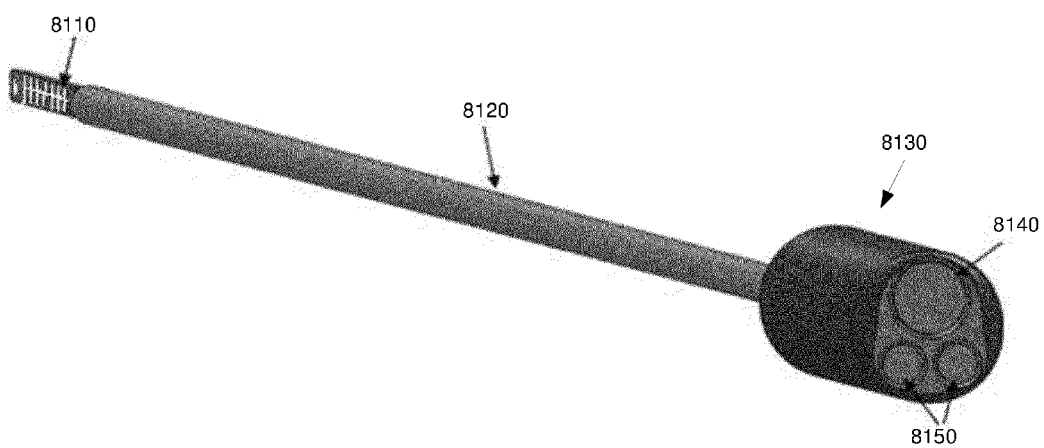

As a non-limiting example, the exemplary embodiment illustrated in FIG. 10 to 12 may have a visual head 8130 having a maximum outer diameter of 10 mm and a maximum length of 60 mm while the maximum outer diameter of the outer shaft 8210 is only 2.8 mm. The visual head 8130 is, apart from the two LEDs 8150, fitted with a camera unit 8140 being a state of the art high definition sensor. Each part of the assembly 8300 is designed to be cleaned and sterilized after each procedure.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A method of assembling a visual system comprising a manipulation device having an insertion portion and a first contact element and being connectable with a visual device having a vision head member and an elongated connector, the method comprising:
   extending a distal end of said insertion portion including a sharp or chamfered distal tip out of an airtight body cavity through an airtight passage from inside said airtight body cavity to outside said airtight body cavity, said airtight passage comprising an internal diameter greater than a maximal diameter of said vision head member;
   connecting said visual device to said manipulation device, said connecting includes slidably mounting a proximal end of said elongated connector into a lumen of said insertion portion while said distal end of said insertion portion including the sharp or chamfered distal tip is extended out of the airtight body cavity; and
   withdrawing said visual device into said cavity through said airtight passage.

2. The method of claim 1, wherein said visual device is a rigid laparoscope or a laparoscopic camera.

3. The method of claim 1, wherein said vision head member comprises at least one of lens, visual signal conductor, digital signal conductor, printed circuit board (PCB), image sensor or illumination source.

4. The method of claim 3, wherein said illumination source is a LED.

5. The method of claim 3, further comprising:
   using the vision head member for collecting, reflecting and/or projecting at least a portion of light created by the illumination source and directing the light towards a target.

6. The method of claim 5, wherein a reflector having a deployable formation is provided for collecting, reflecting and/or projecting the illumination source.

7. The method of claim 6, further comprising:
expanding and contracting the reflector between a smaller diameter and a greater diameter prior for collecting, reflecting and/or projecting the illumination source.

8. The method of claim 7, wherein the reflector has an iris design comprising a plurality of rigid or semi-rigid members.

9. The method of claim 1, wherein said insertion portion has a maximal outer diameter equal or smaller than 3 mm, and wherein said vision head member is at least 5 mm in diameter.

10. The method of claim 1, further comprising:
passing an internal telescopic sleeve into said airtight body cavity through said airtight passage until an end of said internal telescopic sleeve is adjacent to a distal end of the insertion portion, said internal telescopic sleeve comprising a minimal inner diameter equal or greater than a maximal diameter of said vision head member.

11. The method of claim 10, wherein said extension of said distal end of said insertion portion is through said internal telescopic sleeve.

12. The method of claim 1, wherein the elongated connector comprises at least one PCB and/or at least one second contact element disposed on a proximal end thereof.

13. The method of claim 12, wherein said visual system further comprises a control unit and/or a display device, and the method further comprises:
connecting said control unit and/or display device to said insertion portion.

14. The method of claim 13, wherein said connection of said visual device to said manipulation device includes:
connecting said control unit and/or display device to said insertion portion and/or visual device to facilitate direct communication with said at least one second contact element.

15. A method of laparoscopic surgery comprising:
providing a manipulation device having a handheld portion and an insertion portion including a sharp or chamfered distal tip;
providing a visual device having an elongated connector and a visual head member attached to the elongated connector;
extending the insertion portion including the sharp or chamfered distal tip from inside a body cavity to outside of the body cavity while the handheld portion remains outside of the body cavity;
coupling the visual device to the manipulation device by inserting the elongated connector into the insertion portion outside of the body cavity; and
withdrawing the coupled visual device into the body cavity using the handheld portion.

16. The method of claim 15, wherein said vision head member comprises at least one of lens, visual signal conductor, digital signal conductor, printed circuit board (PCB), image sensor or illumination source.

17. The method of claim 15, further providing an airtight passage from inside the body cavity to outside the body cavity and extending the insertion portion of the manipulation device through the airtight passage.

18. The method of claim 17, further comprising:
passing an internal telescopic sleeve into said body cavity through said airtight passage until an end of said internal telescopic sleeve is adjacent to a distal end of the insertion portion, said internal telescopic sleeve comprising a minimal inner diameter equal or greater than a maximal diameter of said vision head member.

19. The method of claim 15, wherein the insertion portion has a maximal outer diameter equal to or smaller than 3 mm, and
wherein said vision head member is at least 5 mm in diameter.

20. The method of claim 15, wherein the elongated connector of the visual device is an elongated printed circuit board (PCB).

* * * * *